United States Patent [19]

Oly

[11] Plant 4,462

[45] Oct. 2, 1979

[54] ROSE PLANT—JAGUAR

[75] Inventor: Hendrik W. Oly, Aalsmeer, Netherlands

[73] Assignee: Jackson & Perkins Company, Medford, Oreg.

[21] Appl. No.: 864,581

[22] Filed: Dec. 27, 1977

[51] Int. Cl.[2] ..... A01H 5/00

[52] U.S. Cl. ..... Plt./28

[58] Field of Search ..... Plt./28

[56] References Cited

U.S. PATENT DOCUMENTS

P.P. 3,724 6/1975 Kordes ..... Plt./28

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

This novel rose variety is a mutation of Mercedes and differs therefrom in its blossom colors which are a slightly darker shade of red than that of the parent variety.

11 Drawing Figures

DETAILED DESCRIPTION OF INVENTION

The present invention relates to a new and distinct variety of rose plant of the floribunda class, which was discovered by me as a cultivated sport of the hybrid tea rose Mercedes (U.S. Plant Pat. No. 3,724), on a plant grown in The Netherlands.

On a Mercedes rose bush, I discovered that flowers on one of the branches were distinctly different from the normal Mercedes in that they were a slightly darker shade of red from bud to open flower. Propagation of the budding eyes on this one stem at Boskoop, The Netherlands, and at Irvine, Calif., proved that this sport came through in successive propagations.

This new cultivar is substantially identical in all respects to its parent, except for the difference in bud and blossom color noted above. The attached drawing shows the stem, leaves, and blossom stages of the new cultivar identified as 519, the normal blossom and buds of the Mercedes cultivar, and the blossom and bud colors of another mutation of Mercedes identified under number 502 and known as Gabriella.

As observed at Irvine, Calif., this new rose variety had bud and blossom coloration in accordance with Royal Horticultural Society Color Chart in the bud of 46A and in the open blossom on the top of the petals with Wilson's Horticultural Color Chart of 819/1 and on the bottom of 820/3.

Being substantially identical to the parent variety except for the aforementioned distinctions, reference is made to U.S. Plant Pat. No. 3,724 for a further description of this variety.

I claim:

1. A new and distinct variety of rose plant of the floribunda class, substantially as herein shown and described, characterized particularly as to novelty by the slightly darker red color of bud and bloom on the plant otherwise identical to the variety Mercedes.

* * * * *

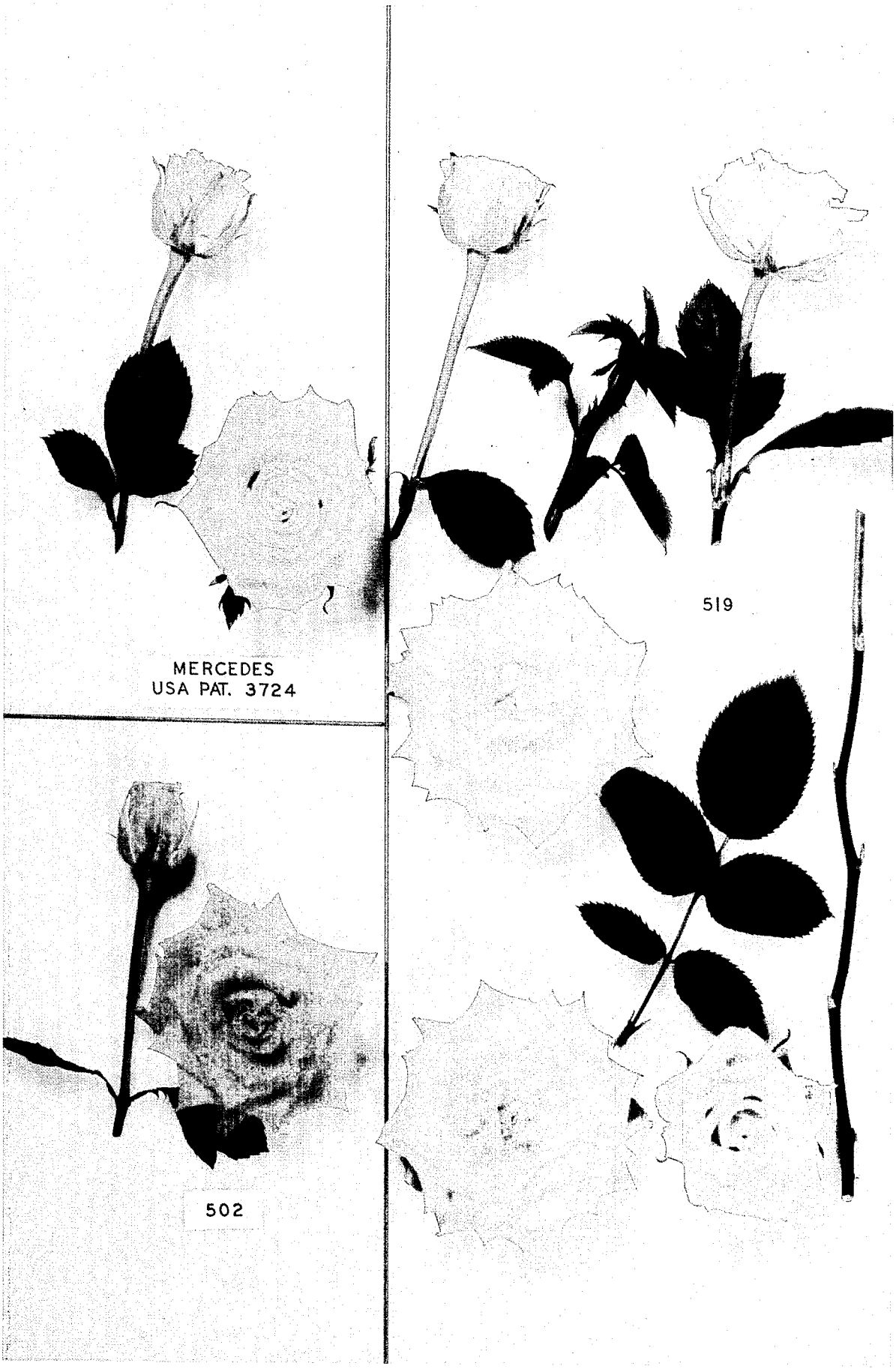
MERCEDES
USA PAT. 3724
519
502